US009215877B2

United States Patent
Santra et al.

(10) Patent No.: US 9,215,877 B2
(45) Date of Patent: Dec. 22, 2015

(54) COMPOSITIONS INCLUDING A VACANCY-ENGINEERED(VE)-ZNO NANOCOMPOSITE, METHODS OF MAKING A COMPOSITION, METHOD OF USING A COMPOSITION

(71) Applicant: University of Central Florida Research Foundation, Inc., Orlando, FL (US)

(72) Inventors: Swadeshmukul Santra, Orlando, FL (US); Megan Berroth, Casselberry, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 0 days.

(21) Appl. No.: 14/173,012

(22) Filed: Feb. 5, 2014

(65) Prior Publication Data

US 2015/0216178 A1 Aug. 6, 2015

(51) Int. Cl.
- *A01N 25/26* (2006.01)
- *A01N 25/28* (2006.01)
- *A01N 59/16* (2006.01)
- *C01G 9/02* (2006.01)

(52) U.S. Cl.
CPC ............ *A01N 59/16* (2013.01); *A01N 25/26* (2013.01); *A01N 25/28* (2013.01); *C01G 9/02* (2013.01); *Y10S 977/773* (2013.01)

(58) Field of Classification Search
None
See application file for complete search history.

(56) References Cited

U.S. PATENT DOCUMENTS

| | | |
|---|---|---|
| 2,913,419 A | 4/1956 | Alexander |
| 3,983,214 A | 9/1976 | Misato et al. |
| 3,992,146 A | 11/1976 | Fazzalari |
| 5,462,738 A | 10/1995 | LeFiles et al. |
| 5,939,357 A | 8/1999 | Jones et al. |
| 6,471,976 B1 | 10/2002 | Taylor et al. |
| 6,548,264 B1 | 4/2003 | Tan et al. |
| 6,924,116 B2 | 8/2005 | Tan et al. |
| 7,147,921 B2 | 12/2006 | Camp et al. |
| 7,163,709 B2 | 1/2007 | Cook et al. |
| 7,226,610 B2 | 6/2007 | Winniczuk |
| 7,332,351 B2 | 2/2008 | Tan et al. |
| 7,850,933 B2 | 12/2010 | Yang et al. |
| 8,221,791 B1 | 7/2012 | Santra |
| 8,246,933 B2 | 8/2012 | Jiang et al. |
| 8,361,437 B2 | 1/2013 | Sharma et al. |
| 2001/0051174 A1 | 12/2001 | Staats |
| 2002/0098529 A1* | 7/2002 | Tan et al. ............... 435/7.21 |
| 2002/0176982 A1* | 11/2002 | Rohrbaugh et al. ....... 428/323 |
| 2004/0067247 A1 | 4/2004 | De Sloovere et al. |
| 2004/0091417 A1 | 5/2004 | Yadav |
| 2005/0084438 A1 | 4/2005 | Do et al. |
| 2006/0018966 A1 | 1/2006 | Lin et al. |
| 2007/0009672 A1 | 1/2007 | Jeong et al. |

(Continued)

OTHER PUBLICATIONS

N Padmavathy, R Vijayaraghavan. Enhanced bioactivity of ZnO nanoparticles-an antimicrobial study. "Science and Technology of Advanced Materials." vol. 9, 2008, pp. 1-7.*

(Continued)

*Primary Examiner* — Isaac Shomer
(74) *Attorney, Agent, or Firm* — William Greener; Alek P. Szecsy; Bond, Schoeneck & King, PLLC

(57) ABSTRACT

Embodiments of the present disclosure, in one aspect, relate to compositions including a vacancy-engineered (VE)-ZnO nanocomposite, methods of making a composition, methods of using a composition, and the like.

14 Claims, 6 Drawing Sheets

(56) References Cited

U.S. PATENT DOCUMENTS

| | | |
|---|---|---|
| 2007/0098806 A1 | 5/2007 | Ismail et al. |
| 2007/0225338 A1 | 9/2007 | Mizell, III et al. |
| 2010/0015236 A1 | 1/2010 | Magdassi et al. |
| 2011/0030151 A1 | 2/2011 | Tremblay et al. |
| 2011/0220577 A1 | 9/2011 | Singh et al. |
| 2011/0244056 A1 | 10/2011 | Santra |

OTHER PUBLICATIONS

Tae-Gon Kim, et al. Silver-Nanoparticle Dispersion From the Consolidation of Ag-Attached Silica Colloid, School of Materials Science and Engineering, Seoul National University, Seoul 151-744, Korea, Oct. 4, 2003, 8 pages.

Yeshchenko, Oleg, Influence of Annealing Conditions on Structure and Optical Properties of Copper Nanoparticles Embedded in Silica Matrix, 2006, Physics Department, National Taras Shevchenko Kyiv University, Ukraine, pp. 1-25.

Kikteva, T.A., Probing the Sol-Gel Conversion in the Tetraethoxysilane/Alcohol/Water System with the Aid of Diffusion-Controlled Flourescence Quenching, 1997, Journal of Colloid and Interface Science, vol. 193, pp. 163-166.

Cho. et al.. "The Study of Antimicrobial Activity and Preservative Effects of Nanosilver Ingredient". Electrochimica Acta 51,956-960 (2005).

Feng, et al. "A Mechanistic Study of the Antibacterial Effect of Silver Ions on *Escherichia coli* and *Staphylococcus aureus*", Journal of Biomedical Materials Research 52, 662-668 (2000).

Jasiorski, et al., "Textile with silver Silica Spheres: its Antimicrobial Activity against *Escherichia coli* and *Staphylococcus aureus*", Journal of Sol-Gel Science and Technology 51, 330-334 (2009).

Lu, et al., "A Simple and Effective Route for the Synthesis of Crystalline Silver Nanrods and Nanowires", Advanced Functional Materials 14, 183-189 (2004).

Solomon, et al. (2007). "Synthesis and study of silver nanoparticles." Journal of Chemical Education. 84, 322-325.

Pal, et al. (2007). "Does the antibacterial activity of silver nanoparticles depend on the shape of the nanoparticle? A study of the gram-negative bacterium *Escherichia coli*." Applied Environmental Microbiology 73, 1712-1720.

Jung, et al. (2008). Antibacterial activity and mechanism of action of the silver ion in *Staphylococcus aureus* and *Escherichia coli*. Applied Environmental Microbiology 74, 2171-2178.

Frisken, B. J. (2001 ). "Revisiting the method of cumulants for the analysis of dynamic light-scattering data." Applied Optics 40, 4087-4091.

Schillinger, et al. (1989). "Antibacterial Activity of Lactobacillus-Sake Isolated from Meal." Applied and Environmental Microbiology 55, 1901-1906.

Rastogi, et al., "Ag colloids and Ag clusters over EDAPTMS-coated silica nanoparticles:synthesis, characterization, and antibacterial activity against *Escherichia coli*." Nanomedicine-Nanotechnology Biology and Medicine 7, 305-314 (2011 ).

Collins, T.J., "ImageJ for Microscopy Biotechniques." 43, 25-30(2007).

Naik, et al., "Biomimetic synthesis and patterning of silver nanoparticles." Nature Materials 1, 169-172 (2002).

Mock, et al., "Shape effects in plasmon resonance of individual colloidal silver nanoparticles." Journal of Chemical Physics 116, 6755-6759 (2002).

Manipradad, et al.; Novel Copper (Cu) Loaded Core-Shell Silica Nanoparticles with Improved Cu Bioavailability: Synthesis, Characterization and Study of Antibacterial Properties; Journal of Biomedical Nanotechnology; vol. 8, 1-9, 2012.

Maniprasad, et al.; Antimicrobial Properties of Copper and Silver Loaded Silica Nanomaterials; Manuscript ID No. 1198620; to be submitted to the 36th International Conference on Advanced Ceramics and Composites (ICACC); Apr. 4, 2012.

H.W. Richardson, "Handbook of Copper Compounds and Applications" Copper Fungicides/batericides H.W. Richardson Editor, 1997, Marcel Dekker, Inc.: New York, NY, pp. 93-122.

Torgeson D.C .. ed. "Fungicides—An Advanced Treatise" Agricultural and Industrial Applications and Enviromental Interaction. vol. 1. 1967. Academic Press: New York. NY, Ch. 6, p. 153-193 [chapter Title: Formulation: Author: E. Somers.

Navarro, E., et al., in "Environmental behavior and ecotoxicity of engineered nanoparticles to algae, plants, and fungi," Ecotoxicology, 2008, 17(5): pp. 372-386.

Oberdorster, G., et al., in Nanotoxicology: An Emerging Discipline Evolving from Studies of Ultrafine Particles, Environmental Health Perspectives, 2005, 113(7): pp. 823-839.

S. Santra, et al., in "Fluorescence Lifetime Measurements to Determine the Core-Shell Nanostructure of FITC-doped Silica Nanoparticles: An Optical Approach to Evaluate Nanoparticle Photostability" Journal of Luminescence, 2006, 117(1) pp. 75-82.

Zhang, K., Synthesis and Characterization of Silica-Copper Oxide Composite Derived from Microemulsion Processing, 1999, Langmuir, vol. 15, pp. 3056-3061.

Zhang, X. A New Solution Route to Hydrogen-terminated Silicon Nanoparticles: Synthesis, Functionalization and Water Stability, Jan. 2007, Nanotechnology, vol. 18, pp. 1-6.

International Search Report and Written Opinion dated Jan. 2, 2011.

Kim, Y.H., et al., "Preparation and characterization of the Antibacterial Cu Nanoparticle Formed on the Surface of SiO2 Nanoparticles," J. Phys. Chem B 2006, vol. 110, pp. 24923-24928.

Bark, T.K., et al., "Nanosilica-From MEdicine to Pest Control," Parasitol, R es 2008, vol. 103, pp. 253-258.

Sebastien Dugravot et al. Dimethyl Disulfide Exerts Insecticidal Neurotixicity Through Mitochondrial Dysfunction and Activation of Insect KATP Channels; Journal of Neurophysiology; 2003; 8 pages.

International Search Form PCT/ISA/220, International Application No. PCT/US2015/012186, p. 1-12, International Application Filed Jan. 21, 2015.

Fakroueian et al., "Influence of Modified ZnO Quantum Dots and Nanostructures As New Antibacterials", Advances in Nanoparticles, 2013, vol. 2, pp. 247-258.

Kumari et al., Jan. 29, 2014, "Self-Assembled Ultra-Small Zinc Stannate Nanocrystals With Mesoscopic Voids Via a Salicylate Templating Pathway and Their Photocatalytic Properties", Royal Society of Chemistry, RSC Advances, Journal, vol. 4, pp. 13626-13634.

Kolodziejczak-Radzimska et al., 2014, "Zinc Oxide-From Synthesis to Application: A Review", MDPI, Journal, Materials, doi:10.3390/ma7042833, pp. 2833-2881.

\* cited by examiner

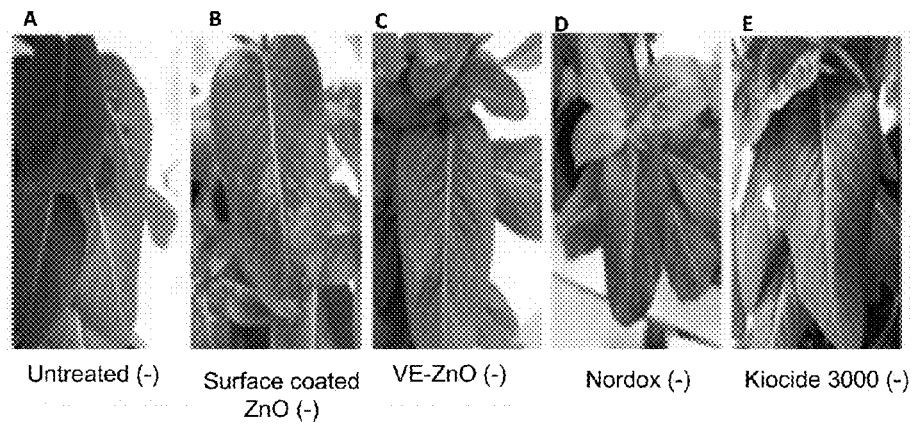
FIG. 3A-E
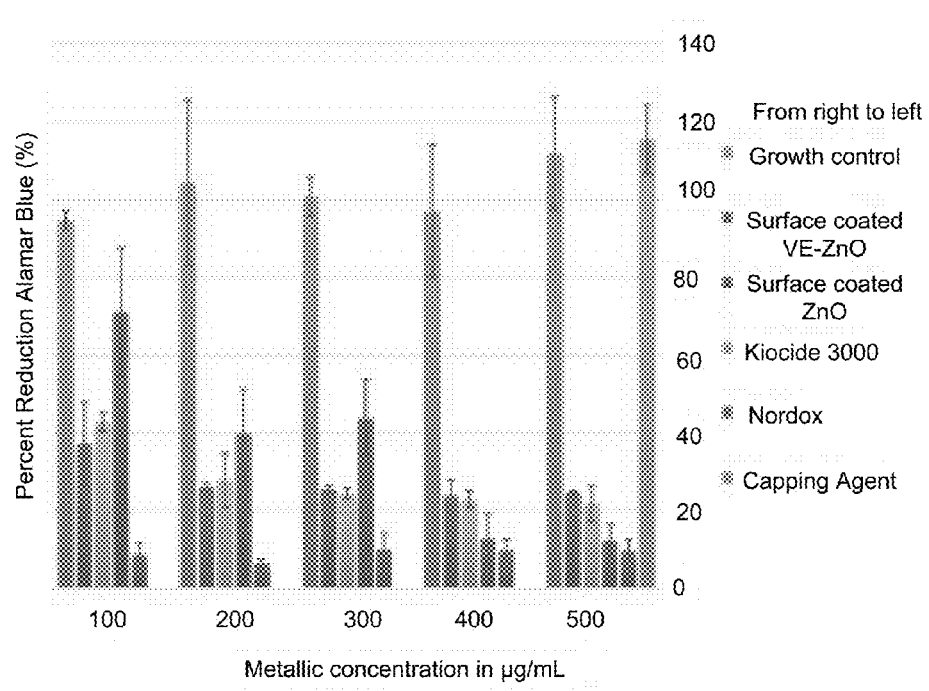
FIG. 4

COMPOSITIONS INCLUDING A VACANCY-ENGINEERED(VE)-ZNO NANOCOMPOSITE, METHODS OF MAKING A COMPOSITION, METHOD OF USING A COMPOSITION

BACKGROUND

The globalization of business, travel and communication brings increased attention to worldwide exchanges between communities and countries, including the potential globalization of the bacterial and pathogenic ecosystem. Bactericides and fungicides have been developed to control diseases in man, animal and plants, and must evolve to remain effective as more and more antibiotic, pesticide and insecticide resistant bacteria and fungi appear around the globe.

Bacterial resistance to antimicrobial agents has also emerged, throughout the world, as one of the major threats to both man and the agrarian lifestyle. Resistance to antibacterial and antifungal agents has emerged as an agricultural issue that requires attention and improvements in the treatment materials in use today.

For example, focusing on plants, there are over 300,000 diseases that afflict plants worldwide, resulting in billions of dollars of annual crop losses. The antibacterial/antifungal formulations in existence today could be improved and made more effective.

SUMMARY

Embodiments of the present disclosure, in one aspect, relate to compositions including a vacancy-engineered (VE)-ZnO nanocomposite, methods of making a composition, methods of using a composition, and the like.

In an embodiment, a composition, among others, includes: a vacancy-engineered (VE)-ZnO nanocomposite including inter-connected VE-ZnO nanoparticles, wherein the VE-ZnO nanoparticles have surface defects associated with oxygen vacancy, wherein the VE-ZnO nanoparticle has a diameter of about 3 to 8 nm, wherein the VE-ZnO nanoparticles include a coating of a surface capping agent having one or more Zn ion chelating functional groups.

In an embodiment, a method, among others, includes: disposing a composition on a surface, wherein the composition has a vacancy-engineered (VE)-ZnO nanocomposite including inter-connected VE-ZnO nanoparticles, wherein the VE-ZnO nanoparticles have surface defects associated with oxygen vacancy, wherein the VE-ZnO nanoparticle has a diameter of about 3 to 8 nm, wherein the VE-ZnO nanoparticles include a coating of a surface capping agent having one or more Zn ion chelating functional groups; and killing a substantial portion of a microorganism or inhibiting or substantially inhibiting the growth of the microorganisms on the surface of a structure or that come into contact with the surface of the structure.

In an embodiment, a method, among others, includes: mixing a water soluble zinc source, a surface capping agent, and an oxidizing agent, wherein the surface capping agent has both a carboxyl group and hydroxyl group; and forming a vacancy-engineered (VE)-ZnO nanocomposite including inter-connected VE-ZnO nanoparticles, wherein the VE-ZnO nanoparticles have surface defects associated with oxygen vacancy, wherein the VE-ZnO nanoparticle has a diameter of about 1 to 10 nm, wherein the VE-ZnO nanoparticles include a coating formed from the surface capping agent.

Other compositions, methods, features, and advantages will be, or become, apparent to one with skill in the art upon examination of the following drawings and detailed description. It is intended that all such additional structures, compositions, methods, features, and advantages be included within this description, be within the scope of the present disclosure, and be protected by the accompanying claims.

BRIEF DESCRIPTION OF THE DRAWINGS

Many aspects of this disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIGS. 3A through E illustrate phytotoxicity results of various coatings.

FIG. 4 illustrates the growth inhibition with Alamar blue Assay of *E. coli* against VE-ZnO, coated ZnO, Nordox, and Kocide 3000.

DETAILED DESCRIPTION

Figure 1A:
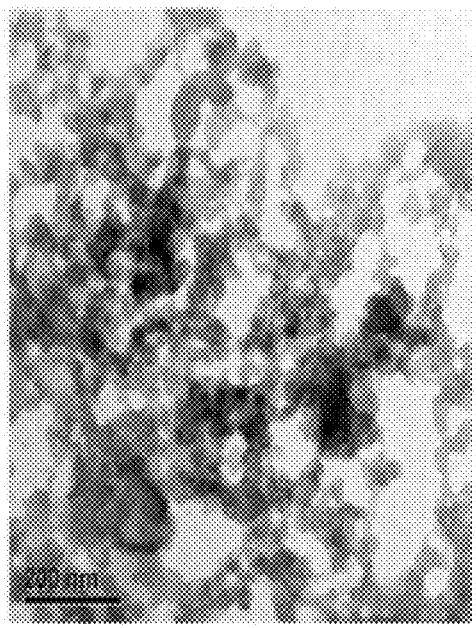
FIGS. 1A and B illustrate HRTEM images of the surface coated VE-ZnO material.

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features that may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, polymer chemistry, biology, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is in atmospheres. Standard temperature and pressure are defined as 25° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

DEFINITIONS

The term "antimicrobial characteristic" refers to the ability to kill and/or inhibit the growth of microorganisms. A substance having an antimicrobial characteristic may be harmful to microorganisms (e.g., bacteria, fungi, protozoans, algae, and the like). A substance having an antimicrobial characteristic can kill the microorganism and/or prevent or substantially prevent the growth or reproduction of the microorganism.

The term "antibacterial characteristic" refers to the ability to kill and/or inhibit the growth of bacteria. A substance having an antibacterial characteristic may be harmful to bacteria. A substance having an antibacterial characteristic can kill the bacteria and/or prevent or substantially prevent the replication or reproduction of the bacteria.

"Gel matrix" or "Nanogel matrix" refers to amorphous gel like substance that is formed by the interconnection of vacancy engineered crystalline zinc oxide nanoparticles (e.g., about 3 to 8 nm) to one another. In an embodiment, the amorphous gel matrix has no ordered (e.g., defined) structure. In an embodiment, the vacancy engineered zinc oxide nanoparticles are interconnected covalently (e.g., through —Zn—O—Zn— bonds), physically associated via Van der Waal forces, and/or through ionic interactions.

"Uniform plant surface coverage" refers to a uniform and complete (e.g., about 100%) wet surface due to spray application of embodiments of the present disclosure. In other words, spray application causes embodiments of the present disclosure to spread throughout the plant surface.

"Substantial uniform plant surface coverage" refers to about 70% or more, about 80% or more, about 90% or more, or more uniform plant surface coverage.

"Substantially covering" refers to covering about 70% or more, about 80% or more, about 90% or more, or more, of the leaves and branches of a plant.

"Plant" refers to trees, plants, shrubs, flowers, and the like as well as portions of the plant such as twigs, leaves, stems, branches, fruit, flowers, and the like. In a particular embodiment, the term plant includes a fruit tree such as a citrus tree (e.g., orange tree, lemon tree, lime tree, and the like).

As used herein, "treat", "treatment", "treating", and the like refer to acting upon a disease or condition with a composition of the present disclosure to affect the disease or condition by improving or altering it. In addition, "treatment" includes completely or partially preventing (e.g., about 70% or more, about 80% or more, about 90% or more, about 95% or more, or about 99% or more) a plant form acquiring a disease or condition. The phrase "prevent" can be used instead of treatment for this meaning. "Treatment," as used herein, covers one or more treatments of a disease in a plant, and includes: (a) reducing the risk of occurrence of the disease in a plant predisposed to the disease but not yet diagnosed as infected with the disease (b) impeding the development of the disease, and/or (c) relieving the disease, e.g., causing regression of the disease and/or relieving one or more disease symptoms.

The terms "bacteria" or "bacterium" include, but are not limited to, Gram positive and Gram negative bacteria. Bacteria can include, but are not limited to, *Abiotrophia, Achromobacter, Acidaminococcus, Acidovorax, Acinetobacter, Actinobacillus, Actinobaculum, Actinomadura, Actinomyces, Aerococcus, Aeromonas, Afipia, Agrobacterium, Alcaligenes, Alloiococcus, Alteromonas, Amycolata, Amycolatopsis, Anaerobospirillum, Anabaena affinis* and other cyanobacteria (including the *Anabaena, Anabaenopsis, Aphanizomenon, Camesiphon, Cylindrospermopsis, Gloeobacter Hapalosiphon, Lyngbya, Microcystis, Nodularia, Nostoc, Phormidium, Planktothrix, Pseudoanabaena, Schizothrix, Spirulina, Trichodesmium,* and *Umezakia* genera) *Anaerorhabdus, Arachnia, Arcanobacterium, Arcobacter, Arthrobacter, Atopobium, Aureobacterium, Bacteroides, Balneatrix, Bartonella, Bergeyella, Bifidobacterium, Bilophila Branhamella, Borrelia, Bordetella, Brachyspira, Brevibacillus, Brevibacterium, Brevundimonas, Brucella, Burkholderia, Buttiauxella, Butyrivibrio, Calymmatobacterium, Campylobacter, Capnocytophaga, Cardiobacterium, Catonella, Cedecea, Cellulomonas, Centipeda, Chlamydia, Chlamydophila, Chromobacterium, Chyseobacterium, Chryseomonas, Citrobacter, Clostridium, Collinsella, Comamonas, Corynebacterium, Coxiella, Cryptobacterium, Delftia, Dermabacter, Dermatophilus, Desulfomonas, Desulfovibrio, Dialister, Dichelobacter, Dolosicoccus, Dolosigranulum, Edwardsiella, Eggerthella, Ehrlichia, Eikenella, Empedobacter, Enterobacter, Enterococcus, Erwinia, Erysipelothrix, Escherichia, Eubacterium, Ewingella, Exiguobacterium, Facklamia, Filifactor, Flavimonas, Flavobacterium, Francisella, Fusobacterium, Gardnerella, Gemella, Globicatella, Gordona, Haemophilus, Hafnia, Helicobacter, Helococcus, Holdemania Ignavigranum, Johnsonella, Kingella, Klebsiella, Kocuria, Koserichia, Kurthia, Kytococcus, Lactobacillus, Lactococcus, Lautropia, Leclercia, Legionella, Lemi-* norella, *Leptospira, Leptotrichia, Leuconostoc, Listeria, Listonella, Megasphaera, Methylobacterium, Microbacterium, Micrococcus, Mitsuokella, Mobiluncus, Moellerella, Moraxella, Morganella, Mycobacterium, Mycoplasma, Myroides, Neisseria, Nocardia, Nocardiopsis, Ochrobactrum, Oeskovia, Oligella, Orientia, Paenibacillus, Pantoea, Parachlamydia, Pasteurella, Pediococcus, Peptococcus, Peptostreptococcus, Photobacterium, Photorhabdus, Phytoplasma, Plesiomonas, Porphyrimonas, Prevotella, Propionibacterium, Proteus, Providencia, Pseudomonas, Pseudonocardia, Pseudoramibacter, Psychrobacter, Rahnella, Ralstonia, Rhodococcus, Rickettsia Rochalimaea Roseomonas, Rothia, Ruminococcus, Salmonella, Selenomonas, Serpulina, Serratia, Shewenella, Shigella, Simkania, Slackia, Sphingobacterium, Sphingomonas, Spirillum, Spiroplasma, Staphylococcus, Stenotrophomonas, Stomatococcus, Streptobacillus, Streptococcus, Streptomyces, Succinivibrio, Sutterella, Suttonella, Tatumella, Tissierella, Trabulsiella, Treponema, Tropheryma, Tsakamurella, Turicella, Ureaplasma, Vagococcus, Veillonella, Vibrio, Weeksella, Wolinella, Xanthomonas, Xenorhabdus, Yersinia*, and *Yokenella*. Other examples of bacterium include *Mycobacterium tuberculosis, M. bovis, M. typhimurium, M. bovis* strain BCG, BCG substrains, *M. avium, M. intracellulare, M. africanum, M. kansasii, M. marinum, M. ulcerans, M. avium* subspecies *paratuberculosis, Staphylococcus aureus, Staphylococcus epidermidis, Staphylococcus equi, Streptococcus pyogenes, Streptococcus agalactiae, Listeria monocytogenes, Listeria ivanovii, Bacillus anthracis, B. subtilis, Nocardia asteroides*, and other *Nocardia* species, *Streptococcus viridans* group, *Peptococcus* species, *Peptostreptococcus* species, *Actinomyces israelii* and other *Actinomyces* species, and *Propionibacterium acnes, Clostridium tetani, Clostridium botulinum*, other *Clostridium* species, *Pseudomonas aeruginosa*, other *Pseudomonas* species, *Campylobacter* species, *Vibrio cholera, Ehrlichia* species, *Actinobacillus pleuropneumoniae, Pasteurella haemolytica, Pasteurella multocida*, other *Pasteurella* species, *Legionella pneumophila*, other *Legionella* species, *Salmonella typhi*, other *Salmonella* species, *Shigella* species *Brucella abortus*, other *Brucella* species, *Chlamydi trachomatis, Chlamydia psittaci, Coxiella burnetti, Escherichia coli, Neiserria meningitidis, Neiserria gonorrhea, Haemophilus influenzae, Haemophilus ducreyi*, other *Hemophilus* species, *Yersinia pestis, Yersinia enterolitica*, other *Yersinia* species, *Escherichia coli, E. hirae* and other *Escherichia* species, as well as other *Enterobacteria, Brucella abortus* and other *Brucella* species, *Burkholderia cepacia, Burkholderia pseudomallei, Francisella tularensis, Bacteroides fragilis, Fudobasctferium nucleatum, Provetella* species, and *Cowdria ruminantium*, or any strain or variant thereof. The Gram-positive bacteria may include, but is not limited to, Gram positive Cocci (e.g., *Streptococcus, Staphylococcus*, and *Enterococcus*). The Gram-negative bacteria may include, but is not limited to, Gram negative rods (e.g., Bacteroidaceae, Enterobacteriaceae, Vibrionaceae, Pasteurellae and Pseudomonadaceae). In an embodiment, the bacteria can include *Mycoplasma pneumoniae*.

The term "protozoan" as used herein includes, without limitations flagellates (e.g., *Giardia lamblia*), amoeboids (e.g., *Entamoeba histolitica*), and sporozoans (e.g., *Plasmodium knowlesi*) as well as ciliates (e.g., *B. coli*). Protozoan can include, but it is not limited to, *Entamoeba coli, Entamoeabe histolitica, Iodoamoeba buetschlii, Chilomastix meslini, Trichomonas vaginalis, Pentatrichomonas homini, Plasmodium vivax, Leishmania braziliensis, Trypanosoma cruzi, Trypanosoma brucei*, and *Myxoporidia*.

The term "algae" as used herein includes, without limitations microalgae and filamentous algae such as *Anacystis nidulans, Scenedesmus* sp., *Chlamydomonas* sp., *Clorella* sp., *Dunaliella* sp., *Euglena so., Prymnesium* sp., *Porphyridium* sp., *Synechoccus* sp., *Botryococcus braunii, Ctypthecodinium cohnii, Cylindrotheca* sp., *Microcystis* sp., *Isochrysis* sp., *Monallanthus salina, M. minutum, Nannochloris* sp., *Nannochloropsis* sp., *Neochloris oleoabundans, Nitzschia* sp., *Phaeodactylum tricornutum, Schizochytrium* sp., *Senedesmus obliquus*, and *Tetraselmis sueica* as well as algae belonging to any of *Spirogyra, Cladophora, Vaucheria, Pithophora* and *Enteromorpha* genera.

The term "fungi" as used herein includes, without limitations, a plurality of organisms such as molds, mildews and rusts and include species in the *Penicillium, Aspergillus, Acremonium, Cladosporium, Fusarium, Mucor, Nerospora, Rhizopus, Tricophyton, Botryotinia, Phytophthora, Ophiostoma, Magnaporthe, Stachybotrys* and *Uredinalis* genera.

DISCUSSION

In accordance with the purpose(s) of the present disclosure, as embodied and broadly described herein, embodiments of the present disclosure, in one aspect, relate to compositions including a vacancy-engineered (VE)-ZnO nanocomposite, methods of making a composition, methods of using a composition, and the like.

In an embodiment, the composition can be used as an antimicrobial agent to kill and/or inhibit the formation of microorganisms on a surface such as a tree, plant, and the like. An advantage of the present disclosure is that the composition is water soluble, film-forming, has antimicrobial properties, and is non-phytotoxic. In particular, the composition is antimicrobial towards *E. coli* and *X. alfalfae* and is non-phytotoxic to ornamental *vinca* sp.

In addition, embodiments of the present disclosure provide for a composition that can be used for multiple purposes. Embodiments of the present disclosure are advantageous in that they can substantially prevent and/or treat or substantially treat a disease or condition in a plant and act as an antibacterial and/or antifungal, while being non-phytotoxic.

In an embodiment, the composition may have an antimicrobial characteristic. The phrase "antimicrobial characteristic" can have the following meaning: kills about 70% or more, about 80% or more, about 90% or more, about 95% or more, or about 99% or more, of the microorganisms (e.g., bacteria) on the surface and/or reduces the amount of microorganisms that form or grow on the surface by about 70% or more, about 80% or more, about 90% or more, about 95% or more, or about 99% or more, as compared to a similar surface without the composition disposed on the surface.

Although not intending to be bound by theory, the unique surface charge and surface chemistry of the VE-ZnO nanoparticles of the VE-ZnO nanocomposite may be responsible for maintaining good colloidal stability. The high surface area and gel-like structural morphology may be responsible for the strong adherence properties to a surface, such as a plant surface. The non-phytotoxicity may be attributed to the neutral pH of the VE-ZnO nanocomposite and limited availability of soluble ions. Additional details are described in the Examples.

In an embodiment, the VE-ZnO nanocomposite can include VE-ZnO nanoparticles such as zinc peroxide ($ZnO_2$) or a combination of ZnO and $ZnO_2$. In an embodiment, the VE-ZnO nanoparticles have surface defects associated with oxygen vacancy, which distinguishes the VE-ZnO nanoparticles from ZnO nanoparticles. UV-Vis studies have shown that VE-ZnO nanoparticles and ZnO nanoparticles have different optical characteristics, which is indicative of showing that VE-ZnO nanoparticles have surface defects associated with oxygen vacancy. Additional details are provided in the Examples.

In an embodiment, the diameter of the zinc oxide nanoparticles can be controlled by appropriately adjusting synthesis parameters, such as amounts of the water soluble zinc source, the surface capping agent, and the oxidizing agent, base, pH, time of reaction, sequence of addition of the components, and the like. For example, the diameter of the particles can be controlled by adjusting the time frame of the reaction. Although not intending to be bound by theory, the superior antimicrobial efficacy of embodiments of the present disclosure can be attributed to the quantum confinement (e.g., size) and surface defect related properties of the VE-ZnO nanoparticle. The size of the VE-ZnO nanoparticle may allow the VE-ZnO nanoparticles to be transported systematically into the plant, reach the phloem tissue, and interact with the pathogen, for example. In an embodiment, the VE-ZnO nanoparticle can have a diameter of about 1 to 10 nm or about 5 nm or the average diameter is about 5 nm.

In an embodiment, the VE-ZnO nanoparticles can be inter-connected to one another to form inter-connected VE-ZnO nanoparticle chains. In an embodiment, the VE-ZnO nanocomposite can include a plurality of VE-ZnO nanoparticle chains, where the chains can be independent of one another or connect to one or more other chains.

In an embodiment, the VE-ZnO nanoparticles include a coating on the surface made of the surface capping agent. In an embodiment, the surface capping agent includes one or more Zn ion chelating functional groups such as carboxyl groups, hydroxyl groups, amines, thiols, and/or a combination of two or more. In an embodiment, the surface capping agent includes a compound having a carboxyl group and hydroxyl group. In an embodiment the surface capping agent is selected from a small molecule capping agent such as sodium salicylate, sodium gluconate, as well as polymers such as chitosan, silica, polyacrylic acid, polyvinyl alcohol, polyacrylamide, polyvinyl pyrrolidine, dextran, polyethelene glycol, dendrimers, and a combination thereof. In an embodiment, the coating can cover the entire surface of the VE-ZnO nanoparticle or a substantial portion (e.g., about 50% or more, about 60% or more, about 70% or more, about 80% or more, about 90% or more, about 95% or more, or about 99% or more, of the surface of the VE-ZnO nanoparticle) of the surface of the VE-ZnO nanoparticle. In an embodiment, the coating can have a thickness of about 0.5 nm to 10 nm.

In an embodiment, the VE-ZnO nanocomposite can include the VE-ZnO nanoparticles in a gel-matrix. In an embodiment, the gel matrix can include a water soluble zinc source, a surface capping agent, and an oxidizing agent. In an embodiment, the surface capping agent can include compounds such as those recited above (e.g., sodium salicylate). In an embodiment, the oxidizing agent can be about 10 to 50 or about 25 to 35, weight percent of the VE-ZnO nanocomposite gel matrix.

In an embodiment, the water soluble zinc source can include a water soluble zinc salt, and organo zinc complexes such as zinc tartarate, zinc citrate, zinc oxalate, zinc acetate, and the like. In an embodiment, the water soluble zinc salt can include zinc nitrate, zinc sulfate, and zinc chloride. In an embodiment, the water soluble zinc source can be about 40 to 80 or about 50 to 70, weight percent of the VE-ZnO nanocomposite gel matrix.

In an embodiment, the oxidizing agent is selected from hydrogen peroxide, chlorine, sodium hypochlorite, and a combination thereof. In an embodiment, the oxidizing agent can be about 10 to 50 or about 25 to 35, weight percent of the VE-ZnO nanocomposite gel matrix.

In an embodiment, the method of making a composition can include mixing a water soluble zinc source, a surface capping agent, and an oxidizing agent. In an embodiment, the components are mixed in an aqueous solution (e.g., deionized water). In an embodiment, the components are mixed at room temperature and after mixing for about 12 to 36 hours, the pH can be adjusted to about 7.5 with a base such as NaOH. In an embodiment, the components can be simultaneously added together or can be sequentially added together. For example, the surface capping agent and the oxidizing agent can be mixed, and optionally with a base. Then the water soluble zinc source can be slowly added dropwise over the course of a few minutes to an hour, while stirring.

In an embodiment, the oxidizing agent can be about 10 to 50 or about 25 to 35, weight percent of the VE-ZnO nanocomposite. In an embodiment, the water soluble zinc source can be about 40 to 80 or about 50 to 70, weight percent of the VE-ZnO nanocomposite. In an embodiment, the oxidizing agent can be about 10 to 50 or about 25 to 35, weight percent of the VE-ZnO nanocomposite.

Once the components are mixed, the VE-ZnO nanocomposite is formed, where the VE-ZnO nanoparticles have a coating formed from the surface capping agent. The composition can be used as prepared or unbound components (e.g., the water soluble zinc source, the surface capping agent, and the oxidizing agent, and base) can be rinsed off so that only the inter-connected VE-ZnO nanoparticles remain. This process can be performed using a single reaction vessel or can use multiple reaction vessels. Addition details are provided in the Examples.

In an embodiment, the composition can be disposed on a surface of a structure. In an embodiment, the structure can include plants such as trees, shrubs, grass, agricultural crops, and the like, includes leaves and fruit. In an embodiment, the composition provides uniform plant surface coverage, substantial uniform plant surface coverage, or substantially covers the plant. In an embodiment, the composition can be used to treat a plant having a disease or to prevent the plant from obtaining a disease.

In an embodiment, the structure can include those that may be exposed to microorganisms and/or that microorganisms can grow on, such as, without limitation, fabrics, cooking counters, food processing facilities, kitchen utensils, food packaging, swimming pools, metals, drug vials, medical instruments, medical implants, yarns, fibers, gloves, furniture, plastic devices, toys, diapers, leather, tiles, and flooring materials. In an embodiment, the structure can include textile articles, fibers, filters or filtration units (e.g., HEPA for air and water), packaging materials (e.g., food, meat, poultry, and the like food packaging materials), plastic structures (e.g., made of a polymer or a polymer blend), glass or glass like structures on the surface of the structure, metals, metal alloys, or metal oxides structure, a structure (e.g., tile, stone, ceramic, marble, granite, or the like), and a combination thereof.

In an embodiment, after the composition is disposed on the surface, the structure may have an antimicrobial characteristic that is capable of killing a substantial portion of the microorganisms (e.g., bacteria such as *E. coli, X. alfalfa*, and *S. aureus*) on the surface of the structure and/or inhibits or substantially inhibits the growth of the microorganisms on the surface of the structure. The phrase "killing a substantial portion" includes killing about 70% or more, about 80% or more, about 90% or more, about 95% or more, or about 99% or more, of the microorganism (e.g., bacteria) on the surface that the composition is disposed on, relative to structure that does not have the composition disposed thereon. The phrase "substantially inhibits the growth" includes reducing the growth of the microorganism (e.g., bacteria) by about 70% or more, about 80% or more, about 90% or more, about 95% or more, or about 99% or more, of the microorganisms on the surface that the composition is disposed on, relative to a structure that does not have the composition disposed thereon.

As mentioned above, embodiments of the present disclosure are effective for the treatment of diseases affecting plants such as citrus plants and trees. In an embodiment, the composition can function as an antibacterial and/or antifungal, specifically, treating, substantially treating, preventing or substantially preventing, plant diseases such as citrus greening (HLB) and citrus canker diseases. The hydroxyl free radicals, zinc ions, and a combination thereof can act as an antibacterial and/or antifungal for a period of time (e.g., from application to days to months). The design of the composition facilitates uniform plant surface coverage or substantially uniform plant surface coverage. In an embodiment, the composition that is applied to plants can have a superior adherence property in various types of exposure to atmospheric conditions such as rain, wind, snow, and sunlight, such that it is not substantially removed over the time frame for use of the composition. In an embodiment, the composition has a reduced phytotoxic effect or is non-phytotoxic to plants.

Embodiments of the present disclosure can applied on the time frames consistent with the effectiveness of the composition, and these time frames can include from the first day of application to about a week, about a month, about two months, about three months, about four months, about five months, about six months, about seven month, or about eight months.

EXAMPLES

Materials and Methods
Formulation Abbreviations:
Z-SG-1
ZPER-SG-1
ZPER-SG-2
ZSAL-SG-2
ZPSAL-SG-3
ZPSAL-SG-4
ZPSAL-SG-5
ZPSAL-SG-6
ZPSAL-SG-7
Detailed Nanoformulation Synthesis Procedure
Z-SG-1, ZPER-SG-1, ZSAL-SG-2, ZPSAL-SG-3 and ZPSAL-SG-4 synthesis procedure:

In a glass beaker, take 50 ml deionized water, 5 ml Zn Nitrate stock solution (59 weight %), add 1M NaOH dropwise under magnetic stirring until pH is 7.5.
Then divide into 5 equal parts:
  Z-SG-1: no treatment
  ZPER-SG-1: add 2 ml hydrogen peroxide (30%)
  ZSAL-SG-2: add 1 ml of sodium salicylate solution (32.8 weight %)
  ZPSAL-SG-3: add 1 ml of sodium salicylate solution (32.8 weight %), wash to remove unbound sodium salicylate solution, add 2 ml hydrogen peroxide (30%)
  ZPSAL-SG-4: add 2 ml hydrogen peroxide (30%), stir for 2 hours, wash to remove unbound hydrogen peroxide, add 1 ml of sodium salicylate solution (32.8 weight %), wash
ZPER-SG-2 and ZPSAL-SG-5 Synthesis Procedure:

In a glass beaker, take 40 ml deionized water, 10 ml hydrogen peroxide (30%) and 5 ml Zn Nitrate stock solution (59 weight %). Adjust pH to 7.5 with 1N NaOH
Then, divide into 2 equal parts
  ZPER-SG-2: no treatment
  ZPSAL-SG-5: add 2.5 ml sodium salicylate solution (32.8 weight %), check pH—adjust to 7, let stir overnight.
ZPSAL-SG-6 Synthesis Procedure (Coated VE-ZnO)**:
**Coted ZnO material is identical to coated VE-ZnO except that it contains no hydrogen peroxide.

In a glass beaker, take 40 ml deionized water, 10 ml hydrogen peroxide (30%), 2.5 ml sodium salicylate solution (32.8 weight %) and 5 ml Zn Nitrate stock solution (59 weight %). Magnetically stir overnight then adjust pH to 7.5 with 1N NaOH (approximately 25 ml)
ZPSAL-SG-7 Synthesis Procedure:

In a glass beaker, take 40 ml deionized water, 10 ml hydrogen peroxide (30%), 2.5 ml sodium salicylate solution (32.8 weight %) and add approximately 20 ml 1N NaOH. Then add dropwise (very carefully and slowly; a few drops per minute) Zn Nitrate solution (59 weight %) under vigorous magnetic stirring until pH is reached to 7.5.

Figure 1B:
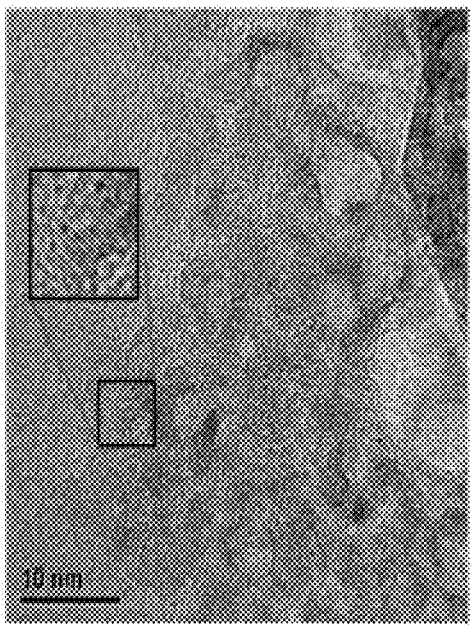

FIGS. 1A and B illustrate HRTEM images of the surface coated VE-ZnO material. In particular, FIG. 1(a) illustrates a representative low-magnification HRTEM image of surface coated VE-ZnO material showing gel-like network of interconnecting quantum size (<5 nm) crystalline VE-ZnO sol particle clusters. FIG. 1(b) illustrates a high-magnification image of VE-ZnO material. The inset shows crystalline lattice fringe of one of VE-ZnO sol particles.

Figure 2A:
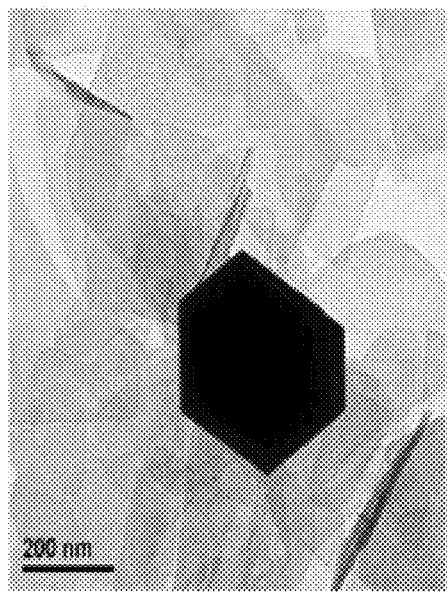
FIGS. 2A and B illustrate HRTEM images of non-VE-ZnO material.
Figure 2B:
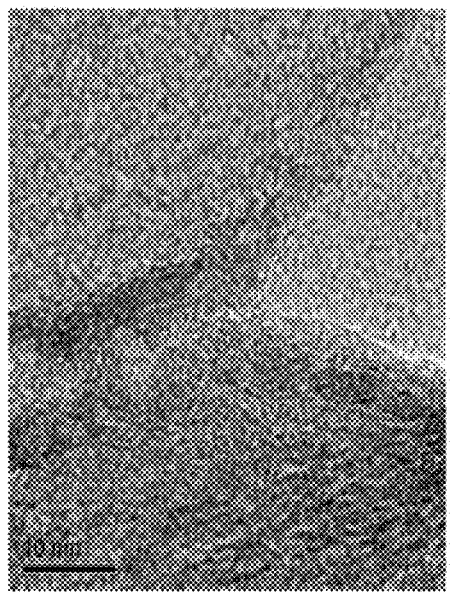

FIGS. 2A and B illustrate HRTEM images of non-VE-ZnO material. In particular, FIG. 2A illustrates a representative HRTEM image of surface coated ZnO material showing plate-like faceted structure in the sub-micron size range. FIG. 2B illustrates a high-magnification image of coated ZnO material shows appearance of both polycrystalline and amorphous regions within a plate structure.

FIGS. 3A through E illustrate phytotoxicity results of various coatings. In particular, FIG. 3 illustrates a phytotoxicity assessment of: (a) uncoated (b) surface coated ZnO, (c) surface coated VE-ZnO, (d) Nordox, and (e) Kocide 3000 materials. Formulations were applied at spray rate of 790 ppm metallic Zn. Digital photographs showing no plant tissue damage (–) occurred even after 72 hours.

FIG. 4 illustrates the growth inhibition with Alamar blue Assay of E. coli against VE-ZnO, coated ZnO, Nordox, and Kocide 3000.

Figure 5:
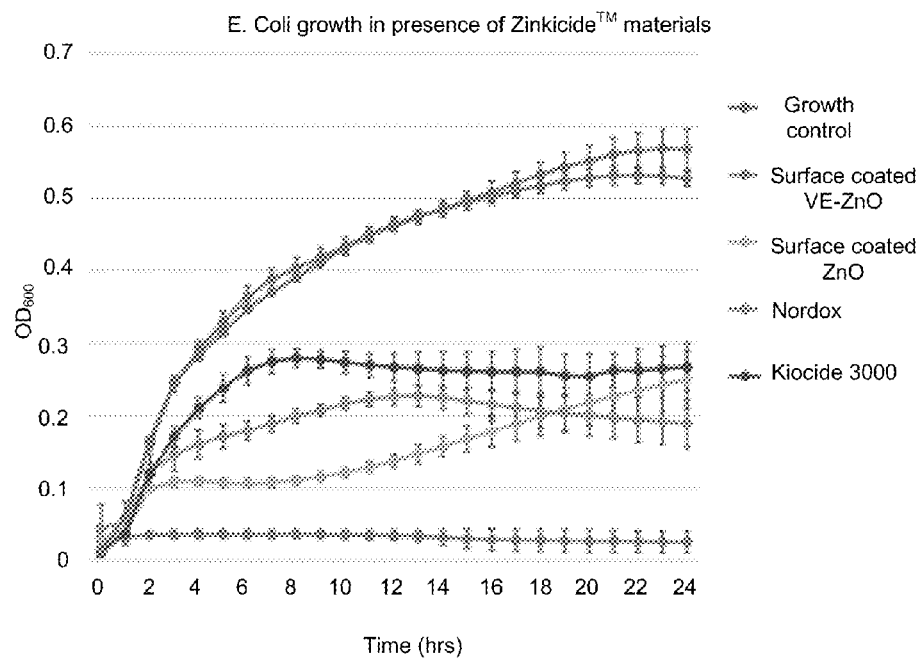
FIG. 5 illustrates *E. coli* growth curves in presence of Zinkicide™ against VE-ZnO, coated ZnO, Nordox, and Kocide 3000.

FIG. 5 illustrates E. coli growth curves in presence of Zinkicide™ of E. coli against VE-ZnO, coated ZnO, Nordox, and Kocide 3000.

Figure 6:
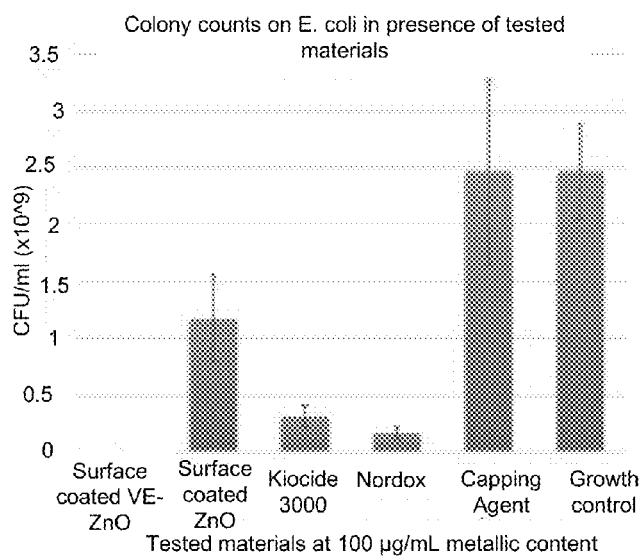
FIG. 6 illustrates *E. coli* viability in presence of Zinkicide™ materials.

FIG. 6 illustrates E. coli viability in presence of Zinkicide™ materials. In particular, FIG. 6 illustrates viability of E. coli against VE-ZnO, coated ZnO, Nordox and Kocide 3000.

Figure 7:
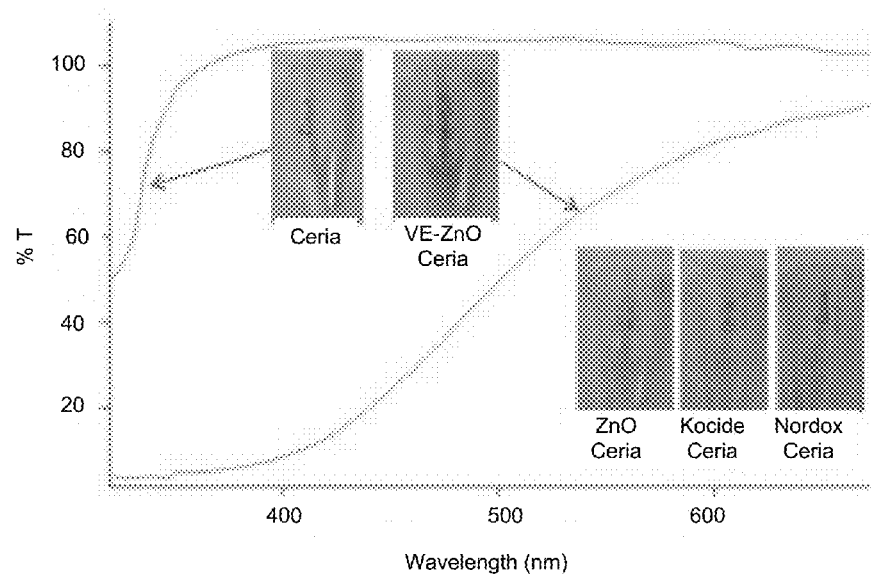
FIG. 7 illustrates direct evidence of ROS generation by the coated VE-ZnO material.

FIG. 7 illustrates direct evidence of ROS generation by the coated VE-ZnO material. FIG. 7 illustrates transmission spectra of mixed-valence ceria and ceria treated with surface coated VE-ZnO material. Ceria and VE-ZnO are whitish in color. However, when combined together an intense red color develops. A clear shift of ceria transmission wavelength towards longer wavelength was observed, confirming conversion of $Ce^{3+}$ to $Ce^{4+}$ state upon reaction with ROS (produced by the surface coated VE-ZnO material).

Figures 8A, 8B:
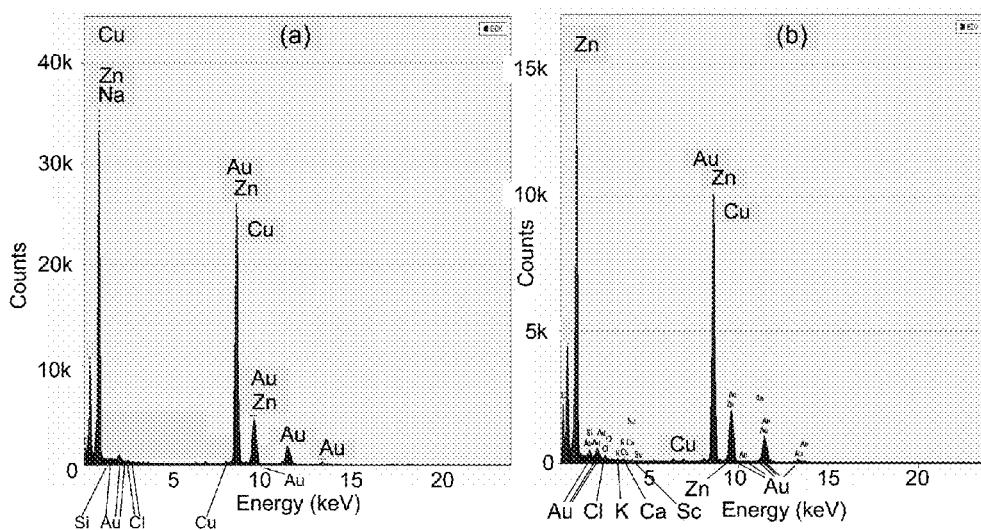
FIGS. 8A and B illustrate HRTEM-EDX spectra of surface coated VE-ZnO and ZnO.

FIGS. 8A and B illustrate HRTEM-EDX spectra of surface coated VE-ZnO and ZnO. FIG. 8 illustrates a representative HRTEM-EDX spectra of surface coated A VE-ZnO and B surface coated ZnO materials. Characteristic elemental peaks of Zn and oxygen were found in the spectra. Au peak is originated from the HRTEM Au grid substrate.

Figures 9A, 9B:
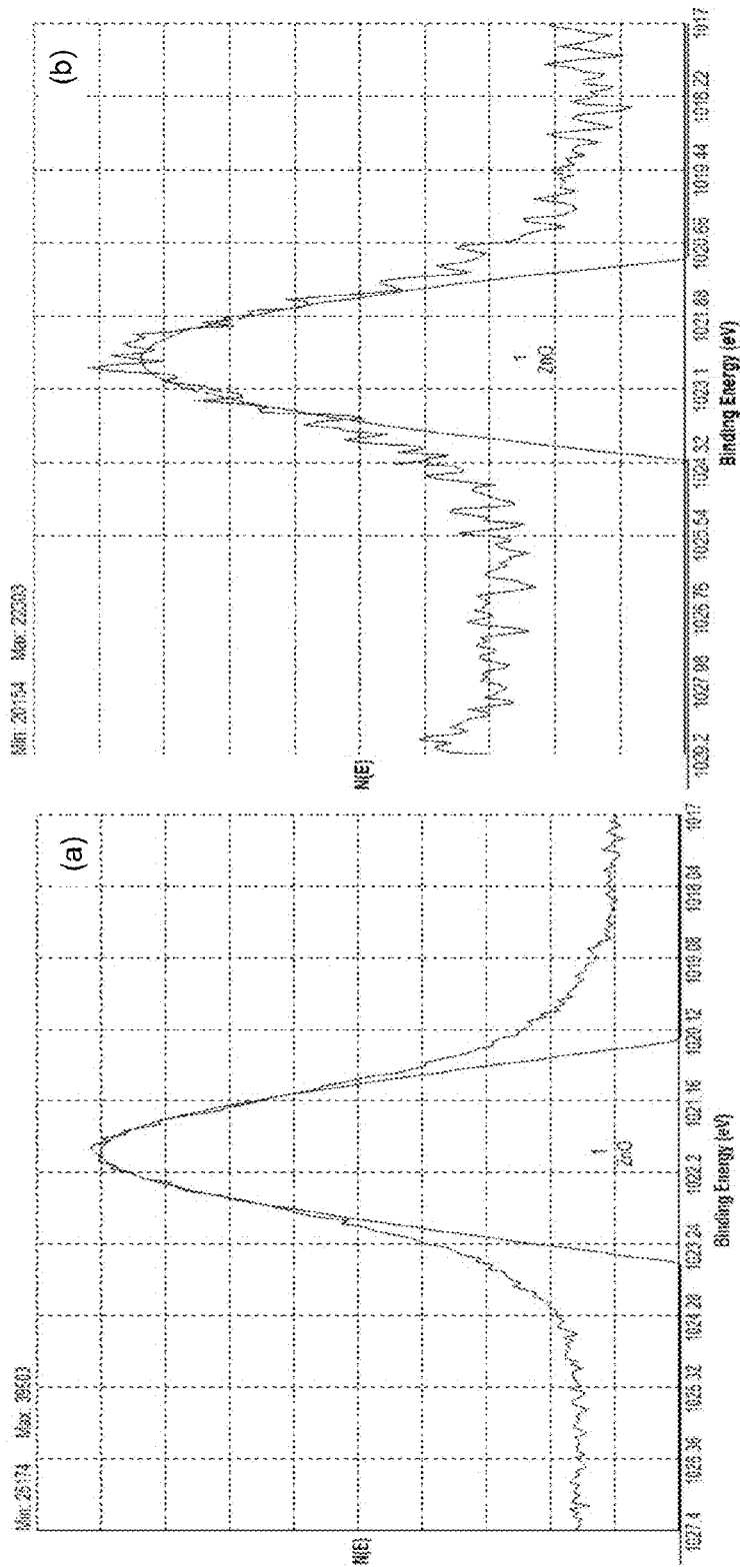
FIGS. 9A and B illustrate x-ray photoelectron spectroscopy (XPS) results of surface coated VE-ZnO and ZnO.

FIGS. 9A and B illustrate x-ray photoelectron spectroscopy (XPS) results of surface coated VE-ZnO and ZnO. In particular, FIG. 9 illustrates XPS results of surface coated: (a) VE-ZnO and (b) surface coated ZnO materials. Characteristic peak of Zn (II) oxidation state was observed.

Figure 10:
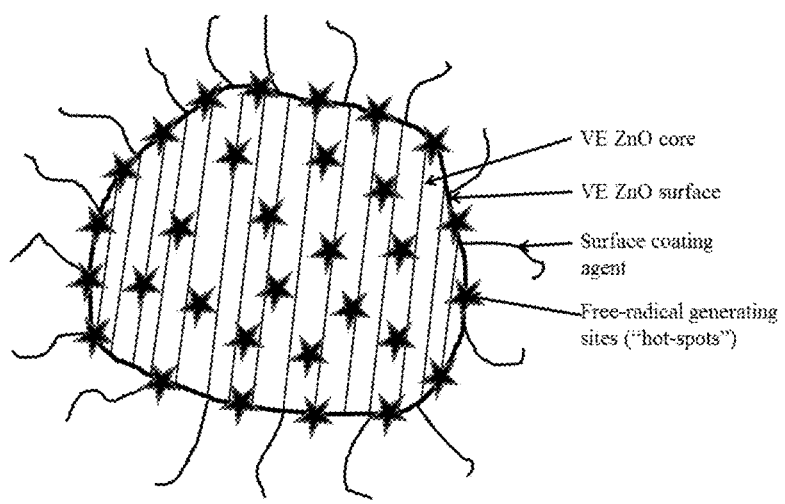
FIG. 10 illustrates a schematic representation of VE ZnO ("Zinkicide") nanoparticle composite (nanocomposite).

FIG. 10 illustrates a schematic representation of VE ZnO ("Zinkicide") nanoparticle composite (nanocomposite).

Table 1 illustrates the minimum inhibitory concentration against *E. coli* for various agents.

TABLE 1

MIC of surface coated VE-ZnO, coated ZnO, surface capping agent, Kocide 3000, and Nordox against *E. coli*

| Tested Material | MIC (µg/mL) in metallic Zn or Cu |
| --- | --- |
| Surface coated ZnO | 750 |
| Surface coated VE-ZnO | 93.75 |
| Capping Agent | 3000 |
| Kocide 3000 | 1000 |
| Nordox | 750 |

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to measurement techniques and the numerical value. In addition, the phrase "about 'x' to 'y'" includes "about 'x' to about 'y'".

Many variations and modifications may be made to the above-described embodiments. All such modifications and variations are intended to be included herein within the scope of this disclosure and protected by the following claims.

Therefore, at least the following is claimed:

1. A gel matrix composition, comprising:
inter-connected vacancy-engineered nanoparticles of zinc oxide (ZnO), zinc peroxide ($ZnO_2$) or a combination thereof, wherein the vacancy-engineered nanoparticles have surface defects associated with oxygen vacancies, wherein the nanoparticles have a diameter of about 3 to 8 nm, wherein the vacancy engineered nanoparticles include a coating of a surface capping agent having both a carboxyl group and hydroxyl group, and wherein the gel matrix composition is prepared at room temperature.

2. The gel matrix composition of claim 1, wherein the surface capping agent is selected from the group consisting of: sodium salicylate, sodium gluconate, and a combination thereof.

3. The gel matrix composition of claim 1, wherein the vacancy-engineered nanoparticles have an average diameter of about 5 nm.

4. The gel matrix composition of claim 1, wherein the coating covers the surface of each of the vacancy-engineered nanoparticles.

5. The gel matrix composition of claim 4, wherein the coating has a thickness of about 0.5 nm to 10 nm.

6. The gel matrix composition of claim 1, further comprising hydrogen peroxide.

7. The gel matrix composition of claim 6, wherein hydrogen peroxide is about 10 to 50 weight percent of the gel matrix composition.

8. The gel matrix composition of claim 6, further comprising sodium hydroxide.

9. The gel matrix composition of claim 8, wherein hydrogen peroxide is about 10 to 50 weight percent of the gel matrix composition and wherein sodium hydroxide is about 10 to 50 weight percent of the gel matrix composition.

10. The gel matrix composition of claim 1, wherein the gel matrix composition has antimicrobial characteristics towards *E. coli* and *X. alfalfae*.

11. The gel matrix composition of claim 1, wherein the gel matrix composition is non-phytotoxic to ornamental *vinca* sp.

12. The gel matrix composition of claim 1, wherein the gel matrix composition is formed by mixing a water soluble zinc source, a surface capping agent, and an oxidizing agent in an aqueous solution at room temperature.

13. The gel matrix composition of claim 12, wherein the oxidizing agent is selected from the group consisting of: hydrogen peroxide, chlorine, sodium hypochlorite and combinations thereof, and wherein the surface capping agent is selected from the group consisting of sodium salicylate, sodium gluconate, and a combination thereof.

14. The gel matrix composition of claim 1, wherein the composition is both antimicrobial and non-phytotoxic.

\* \* \* \* \*